(12) United States Patent
Lee et al.

(10) Patent No.: US 12,014,825 B2
(45) Date of Patent: Jun. 18, 2024

(54) SYSTEM AND METHOD FOR CONVERTING CLINICAL PRACTICE GUIDELINE TO COMPUTER INTERPRETABLE MODEL

(71) Applicant: UNIVERSITY-INDUSTRY COOPERATION GROUP OF KYUNG HEE UNIVERSITY, Gyeonggi-do (KR)

(72) Inventors: Sung Young Lee, Gyeonggi-do (KR); Musarrat Hussain, Gyeonggi-do (KR)

(73) Assignee: UNIVERSITY-INDUSTRY COOPERATION GROUP OF KYUNG HEE UNIVERSITY (KR)

(*) Notice: Subject to any disclaimer, the term of this patent is extended or adjusted under 35 U.S.C. 154(b) by 668 days.

(21) Appl. No.: 16/877,476

(22) Filed: May 18, 2020

(65) Prior Publication Data
US 2021/0012896 A1    Jan. 14, 2021

(30) Foreign Application Priority Data
Jul. 8, 2019    (KR) ........................ 10-2019-0082070

(51) Int. Cl.
G16H 50/20    (2018.01)
G06F 16/383    (2019.01)
G16H 70/20    (2018.01)

(52) U.S. Cl.
CPC .......... *G16H 50/20* (2018.01); *G06F 16/383* (2019.01); *G16H 70/20* (2018.01)

(58) Field of Classification Search
CPC ....... G16H 50/20; G16H 70/20; G06F 16/383
(Continued)

(56) References Cited

U.S. PATENT DOCUMENTS

| 2009/0265188 A1 | 10/2009 | Lamy |
| 2016/0328525 A1 | 11/2016 | Gross |
| 2018/0087102 A1* | 3/2018 | Nagpal ................ C12Q 1/6869 |

(Continued)

FOREIGN PATENT DOCUMENTS

| JP | 2008-514334 | 5/2008 |
| JP | 2013-542749 | 11/2013 |
| JP | 2014-526312 | 10/2014 |

(Continued)

OTHER PUBLICATIONS

Hussain et al., "Recommendation Statements Identification in Clinical Practice Guidelines Using Heuristic Patterns," pp. 152-156, 2018, doi: 10.1109/SNPD.2018.8441036 (Year: 2018).*

(Continued)

*Primary Examiner* — Hiep V Nguyen
(74) *Attorney, Agent, or Firm* — Quarles & Brady LLP

(57) ABSTRACT

A method of converting a clinical practice guideline into a computer-interpretable model includes assigning at least one tag of a recommendation tag and a non-recommendation tag to each of a plurality of sentences extracted by analyzing the clinical practice guideline, filtering out a sentence to which the non-recommendation tag is assigned among the plurality of sentences and extracting a sentence to which the recommendation tag is assigned, identifying whether a phrase of a first element and a phrase of a second element exist in the sentence to which the recommendation tag is assigned based on a knowledge database and mapping and storing the phrase of the first element and the phrase of the second element, and generating a final model by converting the phrase of the first element and the phrase of the second element into a format corresponding to a specific model.

9 Claims, 2 Drawing Sheets

(58) Field of Classification Search
USPC .......................................................... 705/2
See application file for complete search history.

(56) References Cited

U.S. PATENT DOCUMENTS

2019/0179888 A1* 6/2019 Saillet .................... G06N 5/025
2021/0327596 A1* 10/2021 Tahmasebi Maraghoosh .............
G16H 20/00

FOREIGN PATENT DOCUMENTS

| JP | 2015-507782 | 3/2015 |
| JP | 2019-049964 | 3/2019 |
| WO | WO 2019/121130 | 6/2019 |

OTHER PUBLICATIONS

Wikipedia, "Naïve Bayes classifier," published Jun. 17, 2019, available at https://en.wikipedia.org/w/index.php?title=Naive_Bayes_classifier&oldid=902264635 (Year: 2019).*

Gil-Herrera, Eleazar; Classification models in clinical decision making; University of South Florida. ProQuest Dissertations Publishing, 2013. 3604170. (Year: 2013).*

Hematialam et al., "Identifying Condition-Action Statements in Medical Guidelines Using Domain-Independent Features", arXiv preprint arXiv:1706.0420 6v2., disclosed on Jun. 21, 2017.

Hussain et al., "Recommendation Statements Identification in Clinical Practice Guidelines Using Heuristic Patterns", 2018 19th IEEE/ACIS International Conference on SNPD. pp. 152-153, disclosed on Jun. 29, 2018., Busan, Korea.

Office Action for KR10-2019-0082070, issued on Oct. 27, 2020, including English translation, 11 pages.

Notice of Allowance mailed May 27, 2021 with respect to Korean App No. 10-2019-0082070 (with English Translation).

Office Action mailed Jun. 9, 2021 with respect to Japanese App No. 2020-089402 (with English Translation).

Hussain et al., "Information Extraction from Clinical Practice Guidelines: A Step Towards Guidelines Adherence" Department of Computer Science & Engineering, Kyung Hee University, South Korea, published as a Thesis on May 23, 2020.

* cited by examiner

SYSTEM AND METHOD FOR CONVERTING CLINICAL PRACTICE GUIDELINE TO COMPUTER INTERPRETABLE MODEL

CROSS-REFERENCE TO RELATED APPLICATIONS

This application claims priority to and the benefit of Korean Patent Application No. 10-2019-0082070, filed Jul. 8, 2019, the disclosure of which is incorporated herein by reference in its entirety.

BACKGROUND OF THE INVENTION

Field of the Invention

The present invention relates to a method and system for converting a clinical practice guideline into a computer interpretable model, and more specifically, to a method and system for converting a clinical practice guideline, which may be a part of a clinical decision support system that not only can be utilized by a doctor but also helps a doctor in making a clinical decision, into a computer interpretable model.

Description of the Related Art

Clinical Practice Guidelines (CPG) are tools for improving the quality of treatment in medical fields and reducing the variation in treatment depending on each medical doctor. In particular, clinical practice guidelines address decision-making issues for the adequacy of treatment. Therefore, clinical practice guidelines are implemented in the form to provide recommendations, advice, warnings or notifications for specific actions to clinical practitioners.

These clinical practice guidelines represent verification of research results along with the judgment and experience of clinical experts. Extensive clinical practice guidelines are developed to curb clinical practice changes, reduce clinical costs, improve treatment quality, and provide evidence and support to healthcare providers when making clinical decisions.

However, the clinical practice guidelines cause a large gap between clinical study results and actual clinical practice. One of the main causes of the gap between study results and actual clinical practice is due to the text format of clinical practice guidelines.

For this reason, healthcare service providers have difficulty in remembering all relevant clinical practice guidelines and identifying, reviewing and deciding appropriate content within a limited time at the time of treatment.

Conventionally, it is possible to help healthcare service providers in identifying disease-specific contents and making standardized medical decisions by converting clinical practice guidelines into a computer-interpretable format and generating and providing a model.

However, in most of the conventional technologies, not only computer engineers, but also experts in the medical field have converted clinical practice guidelines into computer-interpretable formats to generate a model. That is, the experts in the medical field have explained processes mentioned in the clinical practice guidelines, and the computer engineers have generated a model by converting the clinical practice guidelines into computer-interpretable formats based on the processes of the experts in the medical field.

When the model is generated by converting clinical practice guidelines into the computer-interpretable formats through the above-described method, the accuracy and effectiveness of the model depend on the knowledge and mutual understanding of the experts in the medical field, and thus there is a problem that there is a high possibility of errors in model generation when the knowledge of experts in the medical field lacks knowledge.

SUMMARY OF THE INVENTION

The present invention provides a method and system for converting a clinical practice guideline, which is a part of a clinical decision support system that can be utilized not only by a doctor but also helps a doctor in making a clinical decision, into a computer interpretable model.

In addition, an object of the present invention is to provide a method and system for converting a clinical practice guideline into a computer interpretable model, which easily convert the clinical practice guideline into a computer-understandable format to improve the decision-making ability of stakeholders by increasing the usage of the clinical practice guidelines and facilitate the provision of medical services by observing the latest knowledge and evidence as possible.

In addition, another object of the present invention is to provide a method and system for converting a clinical practice guideline into a computer interpretable model, which strengthen a clinical decision support system by introducing new knowledge to enhance the efficiency of use and increase the sharing and reusability of clinical knowledge.

The objects of the present disclosure are not limited to the above-mentioned objects, and other objects and advantages of the present disclosure which are not mentioned may be understood by the following description, and will be more clearly understood by embodiments of the present disclosure. It will also be readily apparent that the objects and advantages of the disclosure may be realized by means of the instrumentalities and combinations particularly pointed out in the appended claims.

To achieve these objects, a method of converting a clinical practice guideline into a computer-interpretable model includes assigning at least one tag of a recommendation tag and a non-recommendation tag to each of a plurality of sentences extracted by analyzing the clinical practice guideline, filtering out a sentence to which the non-recommendation tag is assigned among the plurality of sentences and extracting a sentence to which the recommendation tag is assigned, identifying whether a phrase of a first element and a phrase of a second element exist in the sentence to which the recommendation tag is assigned based on a knowledge database and mapping and storing the phrase of the first element and the phrase of the second element, and generating a final model by converting the phrase of the first element and the phrase of the second element into a format corresponding to a specific model.

Also, to achieve the these objects, a system of converting a clinical practice guideline into a computer-interpretable model includes a pre-processing unit configured to extract a plurality of sentences by analyzing clinical practice guideline, a document reading unit configured to assign at least one tag of a recommendation tag and a non-recommendation tag to each of the plurality of sentences, filter out a sentence to which the non-recommendation tag is assigned among the plurality of sentences, and extract a sentence to which the recommendation tag is assigned, a mapping unit configured to identify whether a phrase of a first element and a phrase of a second element exist in the sentence to which the recommendation tag is assigned based on a knowledge database and map and store the phrase of the first element and the phrase of the second element, and a conversion unit configured to generate a final model by converting the phrase of the first element and the phrase of the second element into a format corresponding to a specific model.

DETAILED DESCRIPTION OF THE PREFERRED EMBODIMENTS

Figure 1:
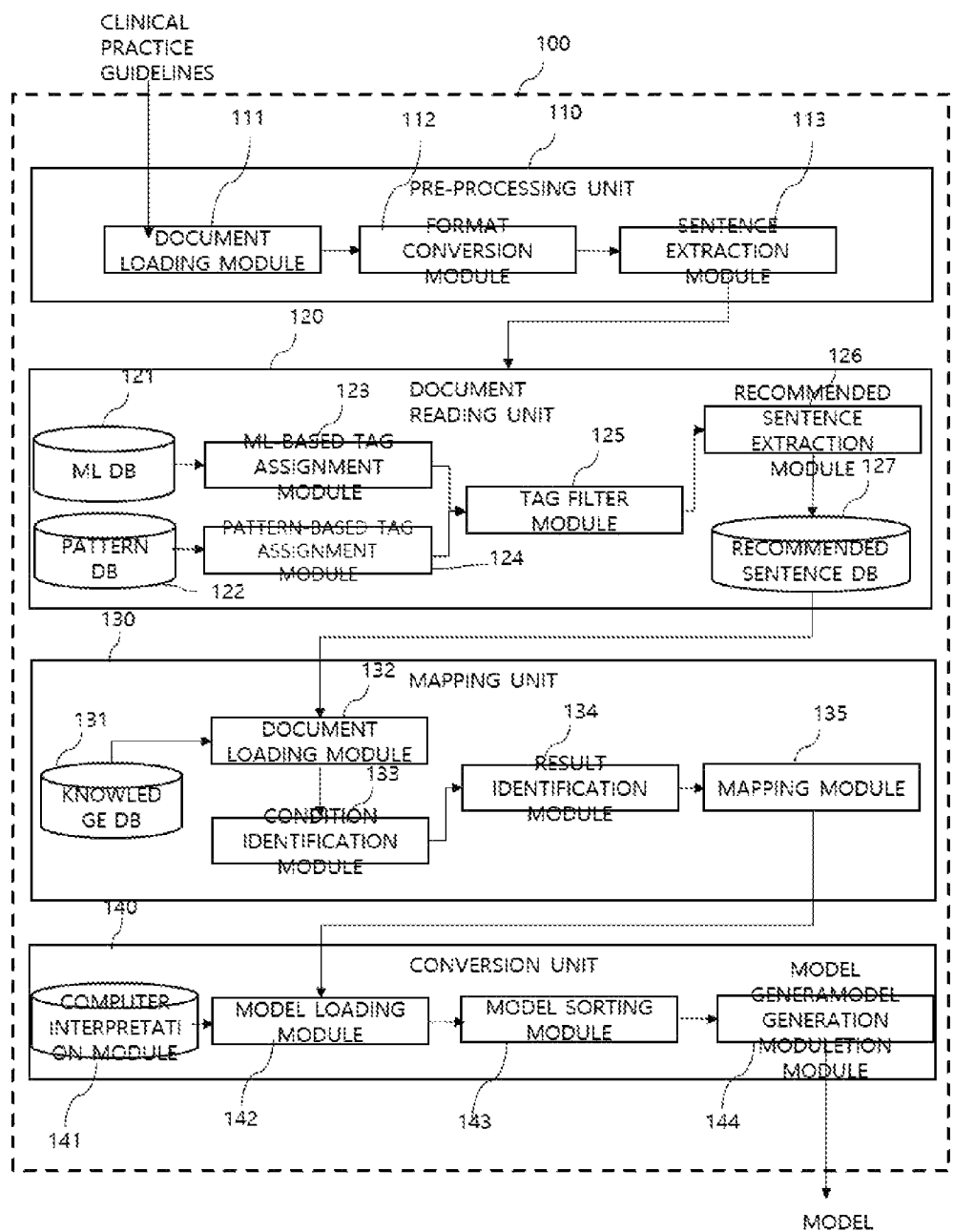
FIG. 1 is a view for describing a system for converting clinical practice guidelines to a computer-interpretable model according to an embodiment of the present invention.

The above-described objects, features, and advantages will be described in detail below with reference to the accompanying drawings, and accordingly, a person skilled in the art to which the present invention pertains can easily implement the technical spirit of the present invention. In describing the present invention, when it is determined that the detailed description of the known technology related to the present invention may unnecessarily obscure the gist of the present invention, the detailed description thereof will be omitted. Hereinafter, preferable embodiments of the present invention will be described in detail with reference to the accompanying drawings. The same reference numbers in the drawings are used to indicate the same or similar components.

Of the terms used in this specification, "a phrase of a first element" means a condition phrase existing in a sentence.

Of the terms used in this specification, "a phrase of a second element" means a result phrase existing in a sentence.

FIG. 1 is a view for describing a system for converting clinical practice guidelines into a computer-interpretable model according to an embodiment of the present invention.

Referring to FIG. 1, a system for converting clinical practice guidelines into a computer-interpretable model includes a pre-processing unit 110, a document reading unit 120, a mapping unit 130, and a conversion unit 140.

The pre-processing unit 110 analyzes the clinical practice guidelines and converts them to a predetermined format (for example, sentences) to extract a plurality of sentences. The pre-processing unit 110 includes a document loading module 111, a format conversion module 112, and a sentence extraction module 113.

The document loading module 111 loads the clinical practice guidelines and provides them to the format conversion module 112.

The format conversion module 112 converts the format of the clinical practice guidelines into plain text when the format of the clinical practice guidelines loaded on the document loading module 111 is not a predetermined format.

The sentence extraction module 113 analyzes the plain text converted by the format conversion module 112 in units of sentences to extract a plurality of sentences. In this case, the sentence extraction module 113 may extract a plurality of sentences by analyzing the plain text in units of sentences through morpheme analysis and syntax analysis.

The document reading unit 120 assigns a recommendation tag or a non-recommendation tag to each of the plurality of sentences extracted by the pre-processing unit 110 and then filters the sentences according to the types of the tags assigned to the plurality of sentences, thus enabling use of the remaining sentences only.

The document reading unit 120 includes an ML database 121, a pattern database 122, an ML-based tag assignment module 123, a pattern-based tag assignment module 124, a tag filter module 125, a recommended sentence extraction module 126, and a recommended sentence database 127.

The ML database 121 includes Naive Bayes, Generalized Liner Model, Deep Learning, Decision Tree, and Random Forest.

A pattern for each annotation is stored in the pattern database 122. That is, information indicating whether each annotation is assigned to a recommended sentence or a non-recommended sentence is stored with respect to annotations in the pattern database 122.

Accordingly, when an annotation assigned to a sentence exists, the pattern-based tag assignment module 124 determines whether the annotation is an annotation assigned to a recommended sentence or an annotation assigned to a non-recommended sentence based on the pattern database 122 and assigns a recommendation tag or a non-recommendation tag to the sentence.

The ML-based tag assignment module 123 assigns a recommendation tag or a non-recommendation tag to each of a plurality of sentences using a classification method stored in the ML database 121. That is, the ML-based tag assignment module 123 may, using a classification method stored in the ML database 121, assign a recommendation tag when a sentence corresponds to a symptom, condition, result, action, and procedure of a specific patient, and assign a non-recommendation tag when the sentence corresponds to general background information.

In one embodiment, the ML-based tag assignment module 123 may assume that there is no relevance occurring between characteristics used to classify sentences into a recommended sentence or a non-recommended sentence using the Naive Bayes stored in the ML database 121, and each characteristic calculate probabilities that a sentence is a recommended sentence and a non-recommended sentence.

Thereafter, the ML-based tag assignment module 123 assigns a tag by determining the type of a sentence that corresponds to a greater probability among a probability that the sentence is a recommended sentence or a probability that the sentence is a non-recommended sentence as the type of the corresponding sentence. That is, the ML-based tag assignment module 123 assigns a recommendation tag to a sentence when the probability of a recommended sentence is greater than a probability of a non-recommended sentence, and assigns a non-recommendation tag to a sentence when the probability of a recommended sentence is less than the probability of a non-recommended sentence.

The pattern-based tag assignment module 124 assigns a recommendation tag or a non-recommendation tag to each of a plurality of sentences using a pattern stored in the pattern database 122. That is, the pattern-based tag assignment module 124 assigns a recommendation tag or a non-recommendation tag according to the annotation of a sentence based on patterns of annotations stored in the pattern database 122.

In one embodiment, the pattern-based tag assignment module 124 may assign a recommendation tag to a corresponding sentence when an annotation is assigned to the sentence and the pattern of the annotation represents a recommended sentence with reference to the pattern database 122.

In another embodiment, the pattern-based tag assignment module 124 may assign a non-recommendation tag to a corresponding sentence when an annotation is assigned to the sentence and the pattern of the annotation represents a non-recommended sentence with reference to the pattern database 122.

As described above, since the ML-based tag assignment module 123 and the pattern-based tag assignment module 124 assign a recommendation tag or a non-recommendation tag to each of a plurality of sentences, one tag or two tags are assigned to each of the plurality of sentences.

The tag filter module 125 filters out a sentence to which a non-recommendation tag of tags assigned to the plurality of sentences is assigned.

In one embodiment, when one tag is assigned to each of the plurality of sentences, the tag filter module 125 filters sentences according to the types of tags assigned to the sentences.

In the above embodiment, the tag filter module 125 filters out a sentence when the type of a tag assigned to the sentence is a non-recommendation tag, and does not filter out a sentence when the type of the tag assigned to the sentence is a recommendation tag.

In another embodiment, when there are two tags assigned to each of a plurality of sentences, the tag filter module 125 filters sentences according to whether the types of the tags assigned to the sentence are identical to or different from each other.

In the above embodiment, the tag filter module 125 filters out a sentence when the types of two tags assigned to the sentence are identical non-recommendation tags, and when the types of two tags assigned to the sentence are different from each other, the tag filter module 125 provides the sentence to the ML-based tag assignment module 123 and the pattern-based tag assignment module 124 such that tags can be assigned again.

Thereafter, the tag filter module 125 filters sentences based on the tags of sentences received from the ML-based tag assignment module 123 and the pattern-based tag assignment module 124, respectively.

The recommended sentence extraction module 126 stores the remaining sentences except the sentences filtered out by the tag filter module 125 among a plurality of sentences in the recommended sentence database 127. Therefore, the sentence to which the recommendation tag is assigned is stored in the recommended sentence database 127.

The mapping unit 130 determines and distinguishes relationships between symptoms, procedures, conditions, and results from a sentence to which the recommendation tag is assigned, the sentence being stored in the recommended sentence database 127 of the document reading unit 120.

The mapping unit 130 includes a knowledge database 131, a sentence loading module 132, a condition identification module 133, a result identification module 134, and a mapping module 135.

The knowledge database 131 stores clinical conditions and results of each sentence. Accordingly, the condition identification module 133 and the result identification module 134 may identify whether a condition phrase and a result phrase each exist in a sentence based on the clinical conditions and results stored in the knowledge database 131.

In addition, the clinical conditions and results stored in the knowledge database 131 are sorted and stored according to relevance of each clinical condition. Accordingly, a specific sentence stored in the knowledge database 131 is associated with the previous sentence and the next sentence.

As described above, the reason why the sentences stored in the knowledge database 131 are sorted and stored according to relevance between the sentences is to enable the mapping module 135 to generate a condition phrase or a result phrase using the previous sentence or the next sentence of the knowledge database 131 when the condition phrase or the result phrase does not exist in the sentence to which the recommendation tag is assigned.

The sentence loading module 132 sequentially loads sentences to which the recommendation tags are assigned and which are stored in the recommended sentence database 127 of the document reading unit 120.

The condition identification module 133 identifies a condition phrase in the sentence to which the recommendation tag is assigned based on the recommended sentence database 127 using the knowledge database 131.

The result identification module 134 identifies a result phrase in the sentence to which the recommendation tag is assigned and which is stored in the recommended sentence database 127 using the knowledge database 131.

The mapping module 135 maps the condition phrase identified by the condition identification module 133 and the result phrase identified by the result identification module 134.

However, the sentence to which the recommendation tag is assigned may or may not include both a condition phrase and a result phrase. That is, the sentence to which the recommendation tag is assigned may include both a condition phrase and a result phrase, or may include either the condition phrases or the result phrase.

As described above, when the sentence to which the recommendation tag is assigned includes both the condition phrase and the result phrase, the condition phrase is identified by the condition identification module 133 and the result phrase is identified by the result identification module 134.

However, when the sentence to which the recommendation tag is assigned includes only the condition phrase, the condition phrase is identified by the condition identification module 133, but the result phrase is not identified by the result identification module 134, and when the sentence to which the recommendation tag is assigned includes only the result phrase, the condition phrase is not identified by the condition identification module 133, and the result phrase is identified by the result identification module 134.

In one embodiment, the mapping module 135 maps and stores the condition phrase identified by the condition identification module 133 and the result phrase identified by the result identification module 134 when the condition phrase identified by the condition identification module 133 and the result phrase identified by the result identification module 134 exist.

In another embodiment, when the condition phrase identified by the condition identification module 133 does not exist and the result phrase identified by the result identification module 134 exists, the mapping module 135 generates the condition phrase by using the previous sentence and the next sentence of the sentence used in the knowledge database 131 when the result identification module 134 identifies the result phrase, and maps and stores the condition phrase and the result phrase identified by the result identification module 134.

In still another embodiment, when the condition phrase identified by the condition identification module 133 exists and the result phrase identified by the result identification module 134 does not exist, the mapping module 135 generates the result phrase by using the previous sentence and the next sentence of the sentence used in the knowledge database 131 when the condition identification module 133 identifies the condition phrase, and maps and stores the result phrase and the condition phrase identified by the condition identification module 133.

The conversion unit 140 performs conversion into a computer-computable model by using the condition phrase and the result phrase mapped by the mapping unit 130. The conversion unit 140 includes a model loading module 142, a model sorting module 143, and a model generation module 144.

The model loading module 142 loads a conversion target model among a plurality of computer-interpretable models. The reason for this is for the model generation module 144 to prescribe a model that is a criterion for converting the condition phrase and the result phrase mapped by the mapping unit 130 into a computer-computable model. In one embodiment of the present invention, the model loading module 142 loads a Ripple Down Rule (RDR) model among a plurality of computer-interpretable models.

The model sorting module 143 sorts the condition phrases and result phrases mapped by the mapping unit 130 according to the conversion target model loaded by the model loading module 142.

In one embodiment, the model sorting module 143 may sort condition phrases according to the similarity of each of the condition phrases. That is, the model sorting module 143 calculates a similarity according to the number of matched words when the words of the condition phrase match each other, and then sorts the condition phrase and the result phrase having a similarity greater than or equal to a certain value into the same group. Accordingly, the first condition phrase and the second condition phrase in the same group will contain similar clinical conditions.

The model generation module 144 generates a ripple down rule model using condition phrases and result phrases sorted by the model loading module 142. The ripple down rule model generated through this process can be understood by both human experts and computers. Here, although the ripple down rule model is used in the present invention, the type of the conversion target model may be changed.

In one embodiment, the model generation module 144 may implement condition phrases and a result phrases in a tree form. To this end, the model generation module 144 may form the condition phrases and result phrases included in the group as child nodes of the same tree.

The ripple down rule model generated through the above process may be used by a healthcare provider to understand and utilize clinical practice guidelines and make clinical decisions. Also, the clinical practice guidelines can be used as knowledge sources for a clinical information system to be useful in making accurate and standardized clinical decisions.

Figure 2:
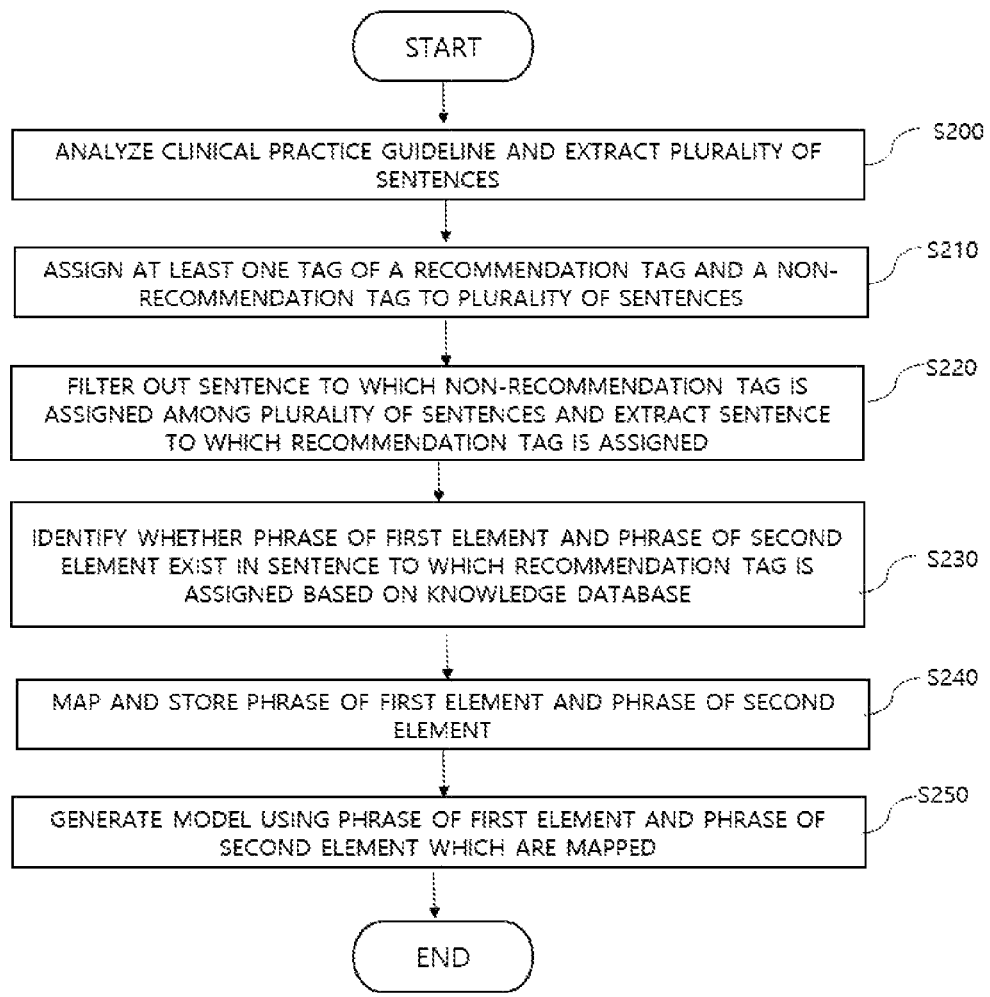
FIG. 2 is a flow chart for describing an embodiment of a method for converting a clinical practice guideline into a computer-interpretable model according to the present invention.

FIG. 2 is a flow chart for describing an embodiment of a method for converting a clinical practice guideline into a computer-interpretable model according to the present invention.

Referring to FIG. 2, a system for converting a clinical practice guideline into a computer-interpretable model analyzes the clinical practice guideline and extracts a plurality of sentences (Step S200).

The system for converting the clinical practice guideline into a computer-interpretable model assigns at least one tag among a recommendation tag and a non-recommendation tag to each of the plurality of sentences which are extracted (Step S210).

The system for converting the clinical practice guideline into a computer-interpretable model filters out sentences to which the non-recommendation tags are assigned among the plurality of sentences and extracts sentences to which the recommendation tags are assigned (Step S220).

In one embodiment of Step S220, when one tag is assigned to each of the plurality of sentences, the system for converting the clinical practice guideline into a computer-interpretable model filters sentences according to the types of tags assigned to the sentences.

In the above embodiment, the system for converting the clinical practice guideline into a computer-interpretable model filters out a sentence when the type of a tag assigned to the sentence is a non-recommendation tag, and does not filter out a sentence when the type of the tag assigned to the sentence is the recommendation tag.

In another embodiment of Step S220, when two tags are assigned to each of the plurality of sentences, the system for converting the clinical practice guideline into a computer-interpretable model filters sentences according to whether the types of tags assigned to the sentences are identical to or different from each other.

In the above embodiment, the system for converting the clinical practice guidelines into a computer-interpretable model filters out a sentence when the types of two tags assigned to the sentence are identical non-recommendation tags, and when the types of two tags assigned to the sentence are different from each other, the tag filter module 125 has the tags assigned again to the sentence.

The system for converting the clinical practice guideline into a computer-interpretable model identifies whether a condition phrase and a result phrase exist in each of the sentences to which the recommendation tags are assigned based on the knowledge database (Step S230).

In this case, the clinical condition and result of each sentence are stored in the knowledge database. Therefore, the system for converting the clinical practice guideline into a computer-interpretable model is capable of identifying whether a condition phrase and a result phrase exist in each of sentences based on clinical conditions and results stored in a knowledge database.

In addition, the clinical conditions and results stored in the knowledge database are sorted and stored according to the relevance of each clinical condition. As described above, the reason why the sentences stored in the knowledge database are sorted and stored according to the relevance with each other is to enable the generation of a condition phrase or a result phrase using the previous sentence or the next sentence of the knowledge database when the condition phrase or the result phrase does not exist in the sentence to which the recommendation tag is assigned.

The system for converting the clinical practice guideline into a computer-interpretable model maps and stores condition phrases and result phrases (Step S240).

In one embodiment of Step S240, the system for converting the clinical practice guideline into a computer-interpretable model maps the condition phrase and the result phrase and stores the same when the condition phrase and the result phrase for each sentence, to which the recommendation tag is assigned, exist based on the knowledge database.

In another embodiment of Step S240, when the condition phrase exists and the result phrase does not exist in each of sentences to which the recommendation tag are assigned, the system for converting a clinical practice guideline into a computer-interpretable model generates a result phrase by using the previous sentence and the next sentence of the sentence used in the knowledge database 131 when the condition phrase is identified, and maps and stores the condition phrase and the generated result phrase.

In another embodiment of step S240, when the condition phrase does not exist and the result phrase exists in each of sentences to which the recommendation tag are assigned, the system for converting a clinical practice guideline into a computer-interpretable model generates a condition phrase by using the previous sentence and the next sentence of the sentence used in the knowledge database 131 when the result phrase is identified, and maps and stores the generated condition phrase and the result phrase.

The system for converting the clinical practice guidelines into a computer-interpretable model converts the condition phrase and the result phrase into a format corresponding to a specific model to generate a final model (Step S250).

According to the present invention as described above, it is possible to be a part of a clinical decision support system that not only can be utilized by a doctor but also helps a doctor in making a clinical decision.

In addition, according to the present invention, it is possible to easily convert the clinical practice guideline into a computer-understandable format to improve the decision-making ability of stakeholders by increasing the usage of the clinical practice guidelines and facilitate the provision of medical services by observing the latest knowledge and evidence as possible.

In addition, according to the present invention, it is possible to strengthen a clinical decision support system by introducing new knowledge to enhance the efficiency of use and increase the sharing and reusability of clinical knowledge.

As described above, although the present invention has been described by the limited embodiments and drawings, the present invention is not limited to the above embodiments, and various modifications and changes will be made from these descriptions by those skilled in the art to which the present invention pertains. Accordingly, the spirit of the present invention should be understood only by the claims set forth below, and all equivalents or equivalent modifications thereof will be said to fall within the scope of the spirit of the present invention.

What is claimed is:

1. A method of converting a clinical practice guideline into a computer-interpretable model comprising:
   assigning at least one tag of a recommendation tag and a non-recommendation tag to each of a plurality of sentences extracted by analyzing the clinical practice guideline, the recommendation tag being generated using a machine learning model;
   assigning a set of alternative tags by a pattern assignment model;
   filtering out a sentence to which the non-recommendation tag is assigned among the plurality of sentences and extracting a sentence to which the recommendation tag is assigned, by a tag filter module, and providing at least a first sentence to the machine learning model and the pattern assignment model in response to identifying a difference between the recommendation tag and the set of alternative tags;
   identifying whether a phrase of a first element and a phrase of a second element exist in the sentence to which the recommendation tag is assigned based on a knowledge database and mapping and storing the phrase of the first element and the phrase of the second element as a computer-interpretable model; and
   generating a final model by converting the phrase of the first element and the phrase of the second element into a format corresponding to a specific model.

2. The method of claim 1, wherein the mapping and storing the phrase of the first element and the phrase of the second element includes:
   mapping and storing the phrase of the first element and the phrase of the second element when the phrase of the first element and the phrase of the second element exist in the sentence to which the recommendation tag is assigned based on the knowledge database, and
   generating a phrase for the one element, which does not exist, based on the knowledge database and mapping and storing the generated phrase and the other of the phrase of the first element and the phrase of the second element when either of the phrase of the first element and the phrase of the second element does not exist in the sentence to which the recommendation tag is assigned.

3. The method of claim 1, wherein the mapping and storing the phrase of the first element and the phrase of the second element includes:
   generating the phrase of the second element using a previous sentence and a next sentence of a sentence used in the knowledge database when the phrase of the first element is identified, and mapping and storing the phrase of the first element and the generated phrase of the second element when the phrase of the first element exists and the phrase of the second element does not exist in the sentence to which the recommendation tag is assigned; and
   generating the phrase of the first element using a previous sentence and a next sentence of a sentence used in the knowledge database when the phrase of the second element is identified, and mapping and storing the generated phrase of the first element and the phrase of the second element when the phrase of the first element does not exist and the phrase of the second element exists in the sentence to which the recommendation tag is assigned.

4. The method of claim 1, wherein the generating the final model by converting the phrase of the first element and the phrase of the second element into the format corresponding to the specific model includes:
   sorting the phrase of the first element and the phrase of the second element according to a conversion target model, and
   generating the final model by using the phrase of the first element and the phrase of the second element which are sorted.

5. The method of claim 1 wherein the machine learning model is configured to assign the recommendation tag when a sentence corresponds to a symptom, condition, result, action, and procedure of a specific patent.

6. The method of claim 5 wherein the machine learning model is configured to assign the non-recommendation tag when the sentence corresponds to general background information.

7. The method of claim 1 wherein the machine learning model is configured to assume that there is no relevance occurring between characteristics used to classify sentences into a recommended sentence or a non-recommended sentence using a Naive Bayes model.

8. The method of claim 1 wherein the machine learning model is stored in a machine learning database.

9. The method of claim 1, further comprising providing a doctor with a suggested treatment technique using the final model to assist in making a clinical decision.

* * * * *